US00PP25199P3

(12) United States Plant Patent
Schoone

(10) Patent No.: US PP25,199 P3
(45) Date of Patent: Dec. 30, 2014

(54) ***PHALAENOPSIS* ORCHID PLANT NAMED 'SPARKLE'**

(50) Latin Name: ***Phalaenopsis* hybrid**
Varietal Denomination: Sparkle

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 101 days.

(21) Appl. No.: 13/573,575

(22) Filed: Sep. 26, 2012

(65) Prior Publication Data

US 2013/0086718 P1 Apr. 4, 2013

Related U.S. Application Data

(60) Provisional application No. 61/450,963, filed on Sep. 29, 2011.

(30) Foreign Application Priority Data

Sep. 30, 2011 (NL) ..... PBR OPS851

(51) Int. Cl.
*A01H 5/00* (2006.01)
*A01H 5/02* (2006.01)

(52) U.S. Cl.
CPC ..... *A01H 5/02* (2013.01)
USPC ..... Plt./311

(58) Field of Classification Search
USPC ..... Plt./311
See application file for complete search history.

*Primary Examiner* — Annette Para
(74) *Attorney, Agent, or Firm* — Foley & Lardner LLP; Sunit Talapatra

(57) ABSTRACT

A new and distinct *Phalaenopsis* plant named 'Sparkle' particularly characterized by flowers which are white with purple spots; the labellum is white with some yellow and purple; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Sparkle'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Sparkle'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Sparkle' is a product of a controlled breeding program conducted by the inventors, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Sparkle' originated from a cross made by the inventor in 1999 in Strengweg, Heemskerk, The Netherlands. The female or seed parent is the *Phalaenopsis* cultivar designated 'Ever Spring', unpatented. The male or pollen parent is the *Phalaenopsis* cultivar designated 'Spanish Melody', unpatented. The new *Phalaenopsis* 'Sparkle' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in July, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Sparkle', which in combination distinguish this *Phalaenopsis* as a new and distinct cultivar:

1. flowers which are white with purple spots; the labellum is white with some yellow and purple;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Sparkle', the female parent 'Ever Spring' has white flowers with large purple marks/spots, the male parent 'Spanish Melody' has pink colored flowers and a red/purple labellum, whereas the flowers of 'Sparkle' are white with purple spots.

Presently, the most commercially similar cultivars to 'Sparkle' are the parental cultivars (especially the female parent), to which a comparison has been provided above.

BRIEF DESCRIPTION OF THE PHOTOGRAPHS

The accompanying photographs illustrate the overall appearance of the new *Phalaenopsis* 'Sparkle' showing the colors as true as is reasonably possible with colored reproductions of this type. Colors in the photographs may differ slightly from the color values cited in the detailed botanical description, which accurately describe the color of 'Sparkle'.

DETAILED BOTANICAL DESCRIPTION

Figure 1:
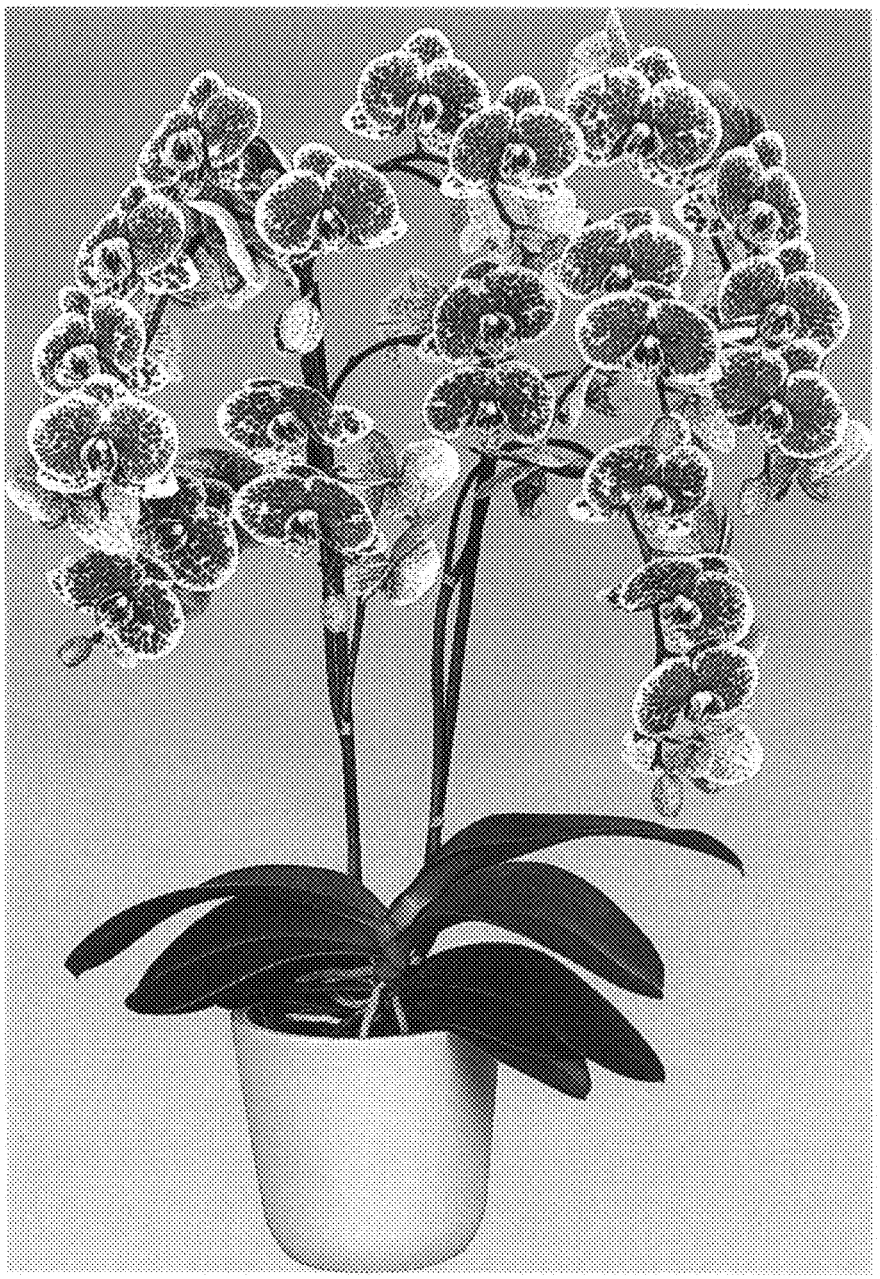
FIG. 1 shows a side view perspective of a typical flowering plant of 'Sparkle' in a 12 cm pot, at 16 months of age.

The new *Phalaenopsis* cultivar 'Sparkle' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Sparkle' as grown in a greenhouse in Strengweg, Heemskerk, The Netherlands, under conditions which closely approximate those generally used in commercial practice. Initially, the ideal temperature to grow plants of 'Sparkle' is 27° C. during the day and at night. Then, during the flowering phase of 'Sparkle', the ideal growing temperature is 20-22° C. during the day and 18° C. at night. Light levels for growing 'Sparkle' are a minimum of 5,000 lux and a maximum of 10,000 lux. A balanced fertilizer with level of 200 ppm N, 87 ppm P, 168 ppm K is applied. Duration of growth of 'Sparkle' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Sparkle' plants described is 12 months after potting.

Classification:

*Botanical.*—*Phalaenopsis* hybrid.

Parentage:

*Female or seed parent.*—*Phalaenopsis* cultivar designated 'Ever Spring', unpatented.

*Male or pollen parent.*—*Phalaenopsis* cultivar designated 'Spanish Melody', unpatented.

Propagation:

*Type.*—Tissue culture.

*Rooting habit and description.*—Fleshy; approximately 2 mm-5 mm wide and green in color (RHS 138C); freely branching. It takes 12 weeks for plants growing in tissue culture to initiate roots.

Plant:

*Size at maturity.*—Height (from bottom of pot to highest flower): about 53 to 65 cm. Spread: about 44 to 75 cm.

*Growth habit.*—Standard; green (RHS N137A) leaves and relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, tip is blunt and asymmetric.

*Texture (both surfaces).*—Smooth and leathery.

*Pubescence.*—None.

*Base.*—Acute.

*Margin.*—Entire.

*Mature leaf length.*—About 12 to 22 cm.

*Mature leaf width.*—About 6 to 10 cm.

*Mature leaf thickness.*—About 1.5 mm.

*Mature leaf color (upper surface).*—Green (RHS N137A).

*Mature leaf color (under surface).*—Green (RHS 138A), edges are a bit purple (RHS N79A).

*Venation.*—Pattern: parallel. Color of mid vein: upper surface: green (RHS N137A), under surface: green (RHS 138A).

Raceme:

*Quantity per plant.*—About 1 to 2.

*Number of flowers per raceme.*—About 5 to 26.

*Length.*—About 58 to 72 cm.

*Diameter.*—About 4 to 6 mm.

*Strength.*—Strong.

*Aspect.*—Upright.

*Texture.*—Glabrous and smooth.

*Color.*—Main color is RHS N200A, spots are green (RHS 143B).

*Internode.*—Length: about 31 to 45 mm.

Inflorescence description:

*Appearance.*—upright to slightly pendant, racemose inflorescence with bilaterally symmetrical flowers that open in succession beginning with the lowermost flower.

*Buds.*—Height (from base to tip): about 15 to 22 mm. Diameter (at midpoint): about 10 to 25 mm. Shape: egg-shaped. Color: main color is yellow/green (RHS 145D), the base and spots are purple (RHS N79A), purple haze (RHS 78C) and some white (RHS NN155C).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
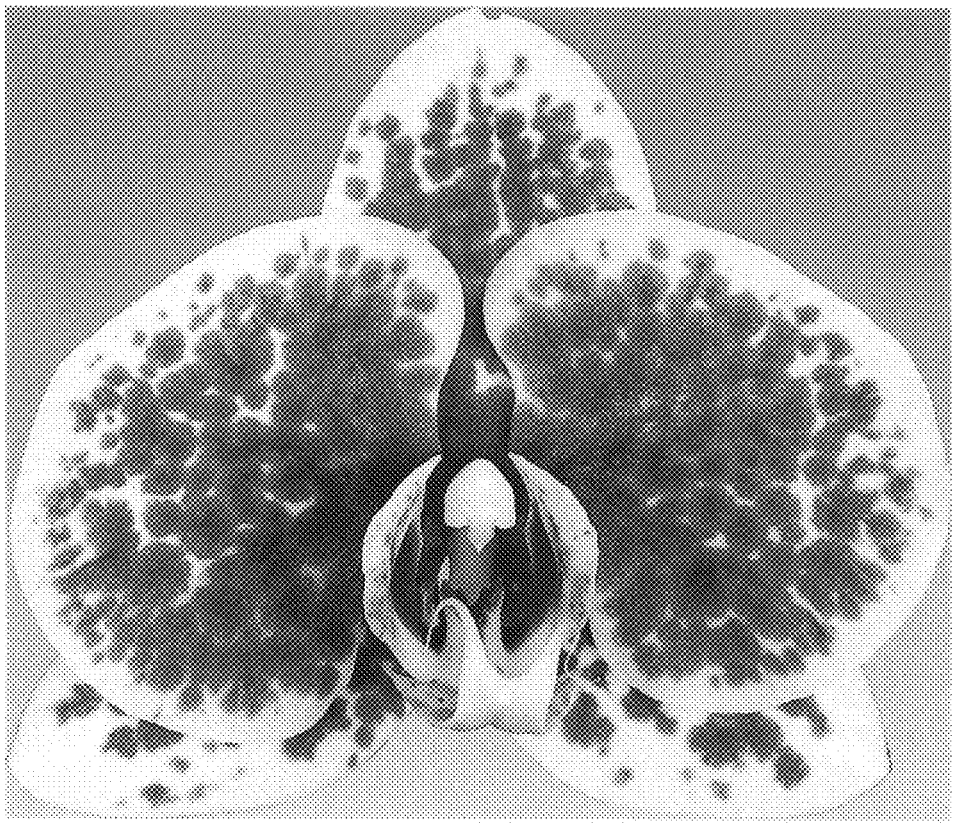
FIG. 2 shows a close-up view of the typical buds and flowers of 'Sparkle'.
Figure 3:
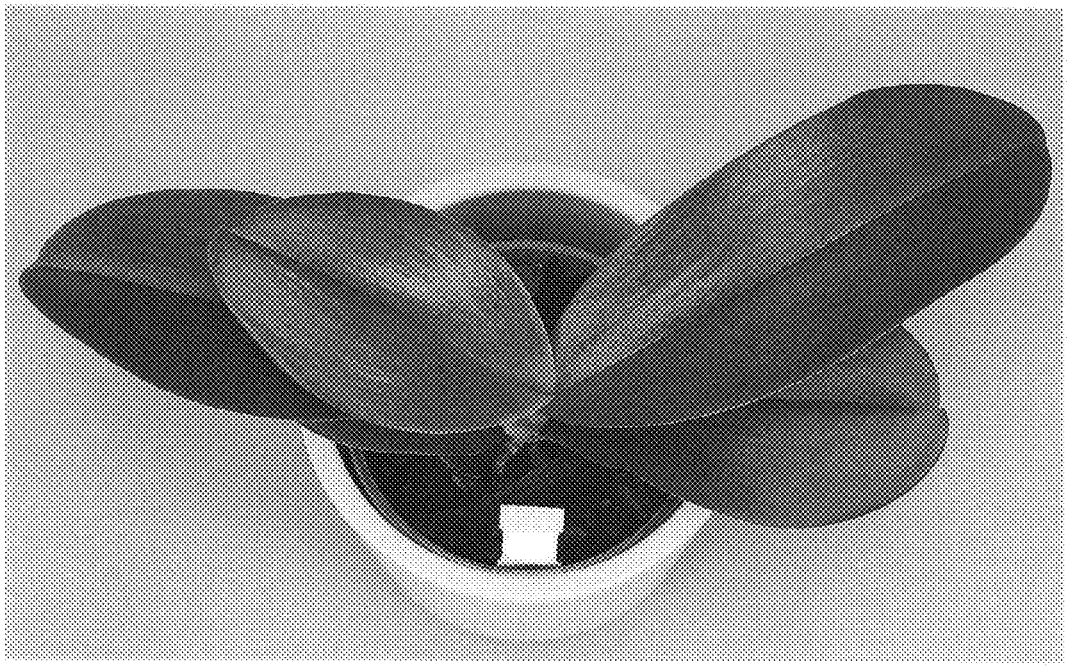
FIG. 3 shows a close-up view of the typical leaves of 'Sparkle'.

*Flower*.—Rate of opening: Flowers fully opened about 2 to 3 days after petal and sepal separation. Orientation at opening: slanted upward and outward. Shape: Typical shape of *Phalaenopsis* Orchid; see FIG. 2. Size (of single bloom): Height: about 50 to 60 mm. Diameter: about 60 to 70 mm. Depth of tube: about 8 mm.

*Petals*.—Quantity and arrangement: three petals and three sepals that are trimerous, overlapping and arranged in 2 whorls. Petals are more pronounced than sepals. Arrangement: Inner whorl comprises 3 petals, 2 lateral petals and labellum. 2 lateral petals: Overall shape: broadly ovate and weakly cupped. Apex: oval. Margin: entire and weakly undulate. Base: broadly ovate. Length: about 45 mm. Width: about 34 mm. Texture: Upper surface: smooth and satiny. Under surface: smooth and satiny. Color (when fully opened): upper surface: Main color is white (RHS NN155C), at the base purple (RHS N79B), purple spots (RHS N79B) with lighter edges (RHS N79C). Under surface: main color is white (RHS NN155C), at the base purple (RHS N79B) and purple spots (RHS N79B) with lighter edges (RHS N79D). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Length: about 21 mm. Width (not flattened): about 16 mm. Texture: Upper & under surface: smooth and satiny. Color (when fully opened): Main color mid lobe is white (RHS NN155C), at the base a little yellow (RHS 3A) with orange/red edges (RHS N34A), spots are purple (RHS 77A) with lighter purple spots and edges (RHS 77B), a red/purple haze (RHS 74C). Under surface: White (RHS NN155C) with purple spots (RHS 77B), edges are orange/red (RHS N34A) with yellow (RHS 3A). Lateral lobes main color is white (RHS NN155C) with a red/purple edge till halfway (RHS 59A). Spots are purple (RHS 77A) with purple edges (RHS 77B). From base a yellow border (RHS 3B) with red/purple spots (RHS 59A). Cirrhi: long. Color: purple and white (RHS N77B & NN155C). Pestle (Callosities): Length: about 8 mm. Width (not flattened): about 5 mm. Height: about 6 mm. Color: White (RHS NN155C) with some yellow (RHS 7A) and on the top some purple (RHS N79A).

*Sepals*.—Arrangement: Outer whorl comprises 3 sepals. Overall shape: elliptical and weakly cupped. Margin: entire and weakly undulate. Length: about 35 to 39 mm. Width: about 24 to 28 mm. Apex: oval; lateral sepals are little pointy and dorsal has a small notch. Texture: Upper & under surface: smooth and satiny. Color (when fully opened): Dorsal sepal: Main color is white (RHS NN155C), at the base some purple and some purple marks (RHS N79B) with lighter edges (RHS N78A). Under surface: at the base and spots are purple (RHS 77A), edges of the spots are white (RHS NN155C) and in the middle purple haze (RHS 76B). Lateral Sepals: Main color is white (RHS NN155C), purple at the base including the spots (RHS N79C). edges of the spots are purple (RHS 77A). It has a yellow/green haze (RHS 1C). Under surface: Main color is white (RHS NN155C), the base and spots are purple (RHS N79C), with purple/violet edges (RHS N81C); it has a yellow/green haze (RHS 1C).

*Pedicel*.—Length: about 31 to 45 mm. Diameter: about 3 mm. Texture: glabrous and smooth. Color: at the base yellow/green (RHS 145D) with red/purple stripe (RHS 70A), In the middle yellow/green (RHS 145D), at the end purple (RHS 76C).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: 9 mm. Diameter: 5 mm. Color: White (RHS N155C), the base and spot are red/purple (RHS 72B).

*Pollinia*.—Quantity: Two. Size: about 1 mm. Color: Orange (RHS 24A).

*Ovary*.—Length: about 3 mm. Diameter: about 4 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Sparkle', as illustrated and described herein.

* * * * *